(12) United States Patent
Leopold et al.

(10) Patent No.: US 8,352,014 B2
(45) Date of Patent: Jan. 8, 2013

(54) SITE MARKER VISIBLE UNDER MULTIPLE MODALITIES

(75) Inventors: Phillip M. Leopold, North Barrington, IL (US); Zachary R. Nicoson, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

(21) Appl. No.: 13/295,825

(22) Filed: Nov. 14, 2011

(65) Prior Publication Data

US 2012/0059256 A1    Mar. 8, 2012

Related U.S. Application Data

(60) Division of application No. 11/561,919, filed on Nov. 21, 2006, now Pat. No. 8,060,183, which is a continuation-in-part of application No. 11/242,334, filed on Oct. 3, 2005, which is a continuation-in-part of application No. 10/964,087, filed on Oct. 13, 2004, now abandoned.

(51) Int. Cl.
  *A61B 5/05*    (2006.01)
(52) U.S. Cl. ........ 600/414; 600/420; 600/426; 600/431; 424/9.1
(58) Field of Classification Search .......... 600/407–437; 424/9.1
See application file for complete search history.

(56) References Cited

U.S. PATENT DOCUMENTS

| | | |
|---|---|---|
| 4,774,957 A | 10/1988 | Nambu et al. |
| 4,991,579 A | 2/1991 | Allen |
| 5,010,145 A | 4/1991 | Ikada et al. |
| 5,016,639 A | 5/1991 | Allen |
| 5,097,839 A | 3/1992 | Allen |
| 5,104,539 A | 4/1992 | Anderson et al. |
| 5,211,164 A | 5/1993 | Allen |
| 5,218,964 A | 6/1993 | Sepponen |
| 5,368,030 A | 11/1994 | Zinreich et al. |
| 5,397,329 A | 3/1995 | Allen |
| 5,427,099 A | 6/1995 | Adams |
| 5,469,847 A | 11/1995 | Zinreich et al. |
| 5,693,085 A | 12/1997 | Buirge et al. |
| 5,730,130 A | 3/1998 | Fitzpatrick et al. |
| 5,769,789 A | 6/1998 | Wang et al. |
| 5,782,764 A | 7/1998 | Werne |

(Continued)

FOREIGN PATENT DOCUMENTS

EP    1491147    12/2004

(Continued)

OTHER PUBLICATIONS

Notice of Allowance dated May 10, 2011 for U.S. Appl. No. 12/133,212.

(Continued)

*Primary Examiner* — Sanjay Cattungal

(74) *Attorney, Agent, or Firm* — Vista IP Law Group LLP

(57) ABSTRACT

A site marker is provided that includes a generally hollow body defining a cavity. A deployment line within the site marker positions at least one marker element within the body portion. The deployment line has a first end that is fixedly secured to a first end of the body portion and a second end that is secured to a second end of the body portion. The deployment line is pre-biased so as to pull the first end of the body portion towards the second end of the body portion, and thereby expand the body portion.

10 Claims, 12 Drawing Sheets

U.S. PATENT DOCUMENTS

| | | | |
|---|---|---|---|
| 5,902,310 A | 5/1999 | Foerster et al. |
| 5,941,890 A | 8/1999 | Voegele et al. |
| 5,961,455 A | 10/1999 | Daum et al. |
| 6,011,987 A | 1/2000 | Barnett |
| 6,015,844 A | 1/2000 | Harvey et al. |
| 6,016,439 A | 1/2000 | Acker |
| 6,056,700 A | 5/2000 | Burney et al. |
| 6,057,700 A | 5/2000 | Crispell |
| 6,173,715 B1 | 1/2001 | Sinanan et al. |
| 6,228,055 B1 | 5/2001 | Foerster et al. |
| 6,231,834 B1 | 5/2001 | Unger et al. |
| 6,261,302 B1 | 7/2001 | Voegele et al. |
| 6,280,385 B1 | 8/2001 | Melzer et al. |
| 6,333,971 B2 | 12/2001 | McCrory et al. |
| 6,350,244 B1 | 2/2002 | Fisher |
| 6,356,782 B1 | 3/2002 | Sirimanne et al. |
| 6,371,904 B1 | 4/2002 | Sirimanne et al. |
| 6,379,379 B1 | 4/2002 | Wang |
| 6,427,081 B1 | 7/2002 | Burbank et al. |
| 6,466,813 B1 | 10/2002 | Shukla et al. |
| 6,544,185 B2 | 4/2003 | Montegrande |
| 6,567,687 B2 | 5/2003 | Front et al. |
| 6,628,982 B1 | 9/2003 | Thomas et al. |
| 6,640,127 B1 | 10/2003 | Kosaka et al. |
| 6,687,533 B1 | 2/2004 | Hirano et al. |
| 6,725,083 B1 | 4/2004 | Burbank et al. |
| 6,766,186 B1 | 7/2004 | Hoyns et al. |
| 6,862,470 B2 | 3/2005 | Burbank et al. |
| 7,611,462 B2 | 11/2009 | Vortman et al. |
| 2001/0049549 A1 | 12/2001 | Boylan et al. |
| 2002/0035324 A1 | 3/2002 | Sirimanne et al. |
| 2002/0082517 A1 | 6/2002 | Klein |
| 2002/0156372 A1 | 10/2002 | Skakoon et al. |
| 2002/0161298 A1 | 10/2002 | Burbank et al. |
| 2002/0188196 A1 | 12/2002 | Burbank et al. |
| 2002/0193815 A1 | 12/2002 | Foerster et al. |
| 2003/0004563 A1 | 1/2003 | Jackson et al. |
| 2003/0097059 A1 | 5/2003 | Sorrell et al. |
| 2003/0139669 A1 | 7/2003 | Montegrande |
| 2003/0199785 A1 | 10/2003 | Hibner et al. |
| 2004/0030237 A1 | 2/2004 | Lee et al. |
| 2004/0030262 A1 | 2/2004 | Fisher et al. |
| 2004/0049224 A1 | 3/2004 | Buehlmann et al. |
| 2004/0093069 A1 | 5/2004 | Priewe et al. |
| 2004/0097981 A1 | 5/2004 | Selis |
| 2004/0105890 A1 | 6/2004 | Klein et al. |
| 2004/0110059 A1 | 6/2004 | Onishi et al. |
| 2004/0116802 A1 | 6/2004 | Jessop et al. |
| 2004/0116805 A1 | 6/2004 | Chesbrough et al. |
| 2004/0116806 A1 | 6/2004 | Burbank et al. |
| 2004/0138555 A1 | 7/2004 | Krag et al. |
| 2005/0033157 A1 | 2/2005 | Klein et al. |
| 2005/0063908 A1 | 3/2005 | Burbank et al. |
| 2005/0277871 A1 | 12/2005 | Selis |
| 2005/0288764 A1 | 12/2005 | Snow et al. |
| 2006/0009712 A1 | 1/2006 | Van Bladel et al. |
| 2006/0079805 A1 | 4/2006 | Miller et al. |
| 2006/0173296 A1 | 8/2006 | Miller et al. |
| 2007/0093726 A1 | 4/2007 | Leopold et al. |
| 2007/0118176 A1 | 5/2007 | Opolski et al. |
| 2007/0167980 A1 | 7/2007 | Figulla et al. |
| 2008/0058715 A1 | 3/2008 | Houser et al. |
| 2008/0269603 A1 | 10/2008 | Nicoson et al. |

FOREIGN PATENT DOCUMENTS

| | | |
|---|---|---|
| EP | 1579878 | 9/2005 |
| EP | 1602341 | 12/2005 |
| EP | 1925266 | 5/2008 |
| WO | WO 00/24332 | 5/2000 |
| WO | WO 01/00101 | 1/2001 |
| WO | WO 01/08578 | 2/2001 |
| WO | WO 02/30482 | 4/2002 |
| WO | WO 2004/012600 | 2/2004 |

OTHER PUBLICATIONS

Response to Non-Final Office Action dated Feb. 17, 2011 for U.S. Appl. No. 12/269,501.
Response to Advisory Action to Place Application in Condition for Allowance dated Feb. 3, 2011 for U.S. Appl. No. 12/133,212.
Response to Final Office Action dated Jan. 4, 2011 for U.S. Appl. No. 11/242,334.
Non-Final Office Action dated Feb. 17, 2011 for U.S. Appl. No. 12/269,501.
Response to Non-Final Office Action dated Dec. 8, 2010 for U.S. Appl. No. 10/964,087.
Final Office Action dated Nov. 23, 2010 for U.S. Appl. No. 12/133,212.
Non-Final Office Action dated Dec. 8, 2010 in U.S. Appl. No. 10/964,087.
Final Office Action dated Jan. 4, 2011 for U.S. Appl. No. 11/242,334.
Response to Final Office Action dated Nov. 23, 2010 for U.S. Appl. No. 12/133,212.
Response to Non-Final Office Action dated Aug. 4, 2010 for U.S. Appl. No. 12/269,501.
Annex to the European Search Report dated Aug. 18, 2010 for EP07254526.
Response to Non-Final Office Action dated Jun. 8, 2010 for U.S. Appl. No. 10/964,087.
Response to Non-Final Office Action dated Jun. 28, 2010 for U.S. Appl. No. 11/242,334.
Non-Final Office Action dated Aug. 4, 2010 for U.S. Appl. No. 12/269,501.
Non-Final Office Action dated Jun. 28, 2010 for U.S. Appl. No. 11/242,334.
Response to Non-Final Office Action dated May 25, 2010 for U.S. Appl. No. 12/133,212.
Non-Final Office Action dated May 25, 2010 for U.S. Appl. No. 12/133,212.
Non-Final Office Action dated Jun. 8, 2010 for U.S. Appl. No. 10/964,087.
Amendment After Final Office Action filed with RCE in response to Advisory Action dated May 6, 2010 for U.S. Appl. No. 10/964,087.
Final Office Action dated Feb. 16, 2010 for U.S. Appl. No. 10/964,087.
Response to Final Office Action dated Feb. 16, 2010 for U.S. Appl. No. 10/964,087.
PCT International Search Report for PCT/US2009/046200 dated Oct. 15, 2009.
Office Action dated Aug. 4, 2009 for U.S. Appl. No. 10/964,087.
Response to Office Action dated Aug. 4, 2009 for U.S. Appl. No. 10/964,087.
PCT International Search Report for PCT/IB2006/053546, dated May 30, 2007.
ACS Industries, Inc. publication entitled "ImagineKnit, We'll Provide It!" Sep. 2003.
Alatassi, Houda et al., "Breast Biopsy Marker Masquerading as a Mass Lesion", The Breast Journal, vol. 11. Nov. 6, 2006 pp. 504-505.
Wahner-Roedler, Dietlind L., "Vacuum-Assisted Breast Biopsy Device (Mammotome) Malfunction Simulating Microcalcifications", The Breast Journal, vol. 11, Nov. 6, 2005, pp. 474-475.
PCT International Search Report for PCT/US2005/034809, dated Jan. 25, 2006.

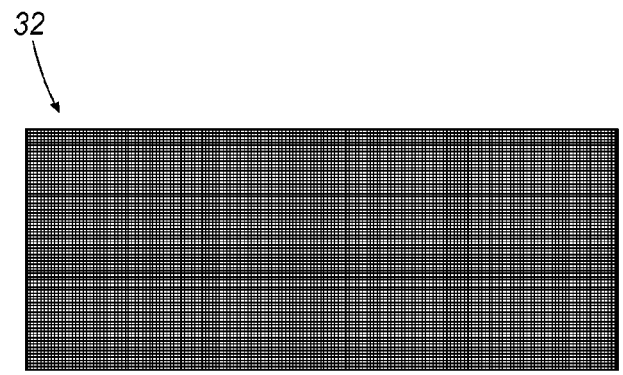
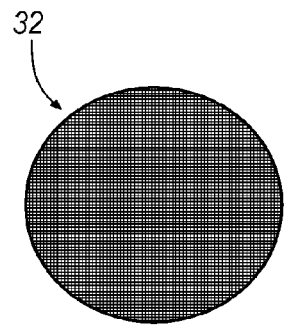
FIG. 4A          FIG. 4B
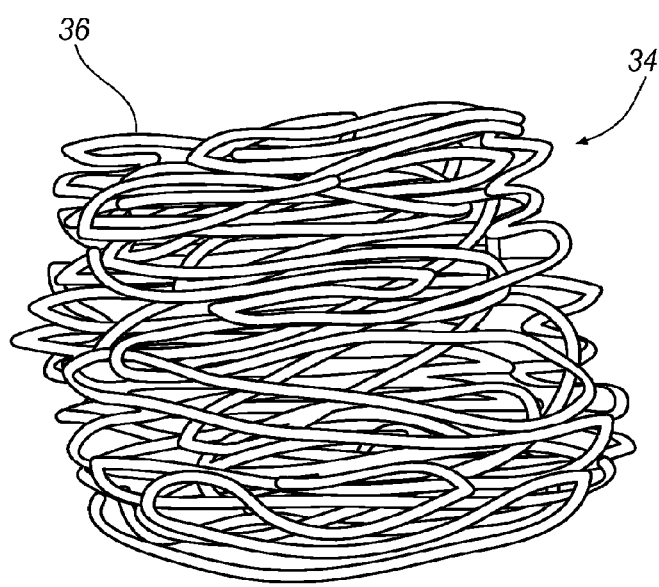
FIG. 5

SITE MARKER VISIBLE UNDER MULTIPLE MODALITIES

CROSS REFERENCE TO RELATED APPLICATIONS

The present application is a continuation of U.S. application Ser. No. 11/561,919, filed Nov. 21, 2006, which is a continuation-in-part of U.S. application Ser. No. 11/242,334, filed Oct. 3, 2005, which is a continuation-in-part of U.S. application Ser. No. 10/964,087, filed Oct. 13, 2004, the priorities of which are claimed under 35 U.S.C. §120, and the contents of which are incorporated herein by reference in their entirety, as though set forth in full.

FIELD OF THE INVENTION

The present invention relates generally to site markers for breast biopsy procedures. More specifically, the present invention relates to site markers that are visible under multiple modalities.

BACKGROUND OF THE INVENTION

In the diagnosis and treatment of breast cancer, it is often necessary to perform a biopsy to remove tissue samples from a suspicious mass. The suspicious mass is typically discovered during a preliminary examination involving visual examination, palpation, X-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by an open surgical technique, or through the use of a specialized biopsy instrument. To minimize surgical intrusion, a small specialized instrument such as a biopsy needle is inserted in the breast while the position of the needle is monitored using fluoroscopy, ultrasonic imaging, X-rays, MRI or other suitable imaging techniques.

In a relatively new procedure, referred to as stereotactic needle biopsy, the patient lies on a special biopsy table with her breast compressed between the plates of a mammography apparatus and two separate X-rays are taken from two different points of reference. A computer then calculates the exact position of the mass or lesion within the breast. The coordinates of the lesion are then programmed into a mechanical stereotactic apparatus which advances the biopsy needle into the lesion with precision. At least five biopsy samples are usually taken from locations around the lesion and one from the center of the lesion.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, and the original features of the tissue may have been removed or altered by the biopsy, it is desirable to insert a site marker into the surgical cavity to serve as a landmark for future identification of the location of the lesion.

Known biopsy site markers have been found to have disadvantages in that the site markers are not visible under all available modalities. Moreover, because of this problem, when cancer is found at a biopsy site that has been previously marked with a site marker, due to the poor visibility of the biopsy site marker under ultrasound or other visualization modalities, the patient must undergo an additional procedure that places an additional device the biopsy site to enable the surgeon to find the biopsy site in subsequent procedures. One known technique has been to place a breast lesion localization wire at the biopsy site. The localization wire is typically placed at the biopsy site via mammography and/or ultrasound.

Accordingly, there is a need for site markers made from biocompatible materials that are visible under various modes of imaging to reduce the number of procedures that patients must undergo in detection and treatment of cancer.

SUMMARY OF THE INVENTION

A site marker is provided that includes a generally hollow body defining a cavity. The site marker is formed into a predeployment configuration whereby the site marker is compressed into a predetermined size and shape to as to be readily positionable within a deployment device. The site marker expands from the first predeployment position to a second post deployment configuration upon insertion into the body. A thread or deployment line (e.g., thread, filament, wire) is attached to and extends between a forward end and a rearward end of the body portion. At least one marker element with a through opening (e.g., ring, tube, helical shape) is included. Accordingly, the deployment line is received in the through opening such that the marker element may selectively slide along the deployment line. This limits migration of the marker element within a body. In another embodiment, a site marker is provided with a filament that may be used either alone or in addition to a deployment line to further hold the marker element in place at an end of the site marker. In yet another embodiment, a deployment line is a hollow tube, and a marker element is able to fit inside of the hollow deployment line.

BRIEF DESCRIPTION OF THE DRAWINGS

These and other features and advantages of the invention will be apparent from the following detailed description and the appended claims, taken in conjunction with the accompanying drawings, in which:

FIG. 4A is a side elevational view of a site marker according to a third embodiment of the present invention;

FIG. 4B is an end elevational view of the site marker of FIG. 4A;

FIG. 5 is a front elevational view of a site marker according to a fourth embodiment of the present invention;

DETAILED DESCRIPTION OF THE INVENTION

Figure 1:
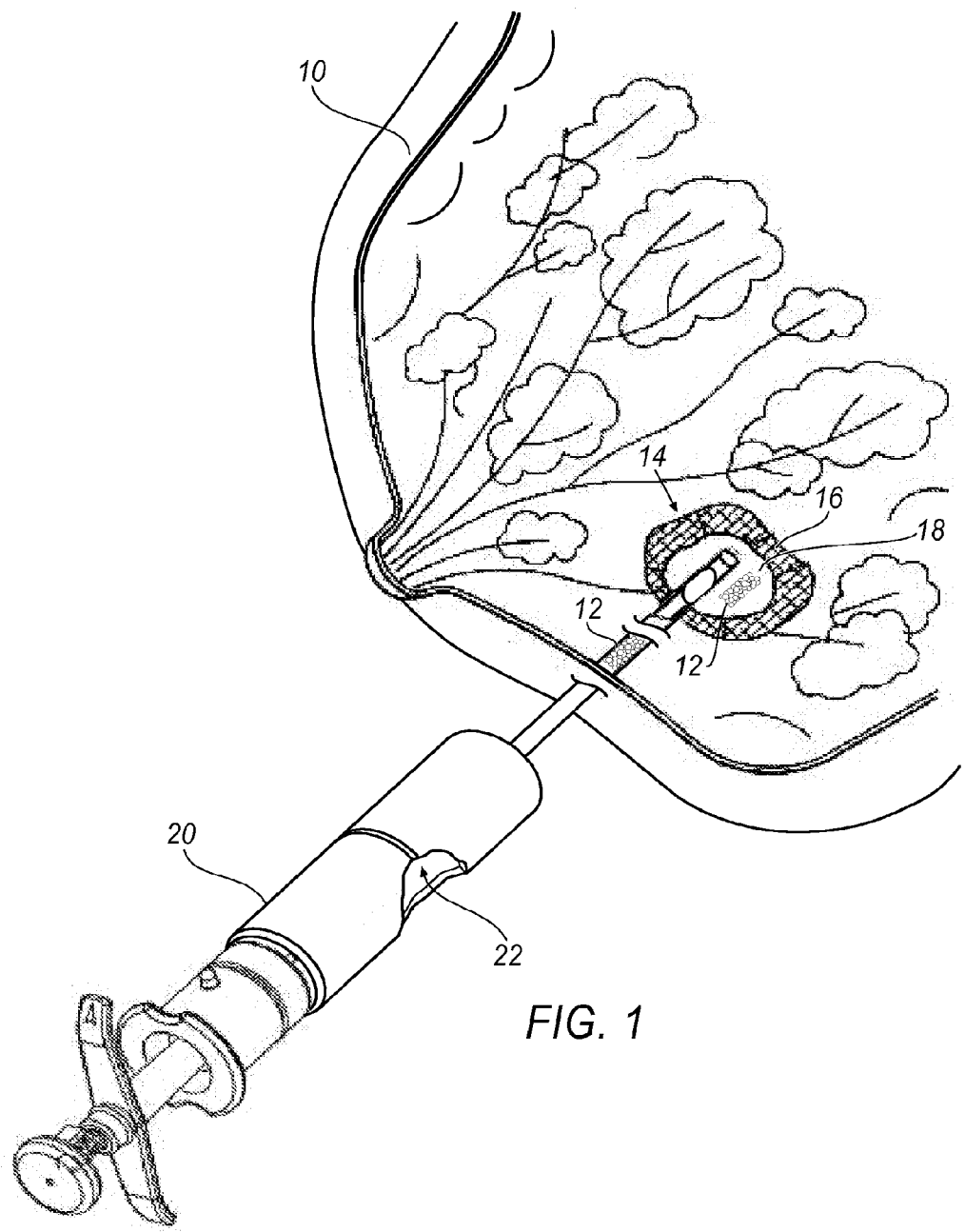
FIG. 1 is a perspective view of a biopsy site in a human breast showing the breast in section and one or more site markers being implanted in the biopsy cavity using a site marker delivery system.

FIG. 1 illustrates a perspective view of a human breast 10 being implanted with a site marker 12 according to an embodiment of the present invention. At a biopsy site 14 is a lesion 16 from which a tissue sample has been removed, resulting in a biopsy cavity 18. One or more site markers 12 are implanted in the biopsy cavity 18 using a marker delivery system 20, as shown in FIG. 1. In one embodiment, the marker delivery system 20 is slidably advanced through an inner lumen 22 of a biopsy device (not shown), which avoids the need to withdraw the biopsy device and thereafter insert the marker delivery system 20. Delivering the site marker 12 in the biopsy cavity 18 without withdrawing the biopsy device reduces the amount of tissue damage and enables more accurate placement of the site marker 12. The marker delivery system 20 illustrated in FIG. 1 is exemplary only and it is understood that the site marker embodiments disclosed herein are suitable for use with other marker delivery systems.

FIGS. 2A-8B illustrate suitable exemplary site marker embodiments according to the present invention. In general, the site markers described herein are made from biocompatible materials such as, but not limited to, titanium, stainless steel, and platinum. These materials have appropriate densities for radiographic imaging, appropriate surface characteristics for ultrasonic imaging, and appropriate magnetic characteristics for magnetic resonance imaging. The site markers that will be described below are preferably made from titanium; however, it is understood that any suitable biocompatible material may be used.

Figures 2A, 2B:
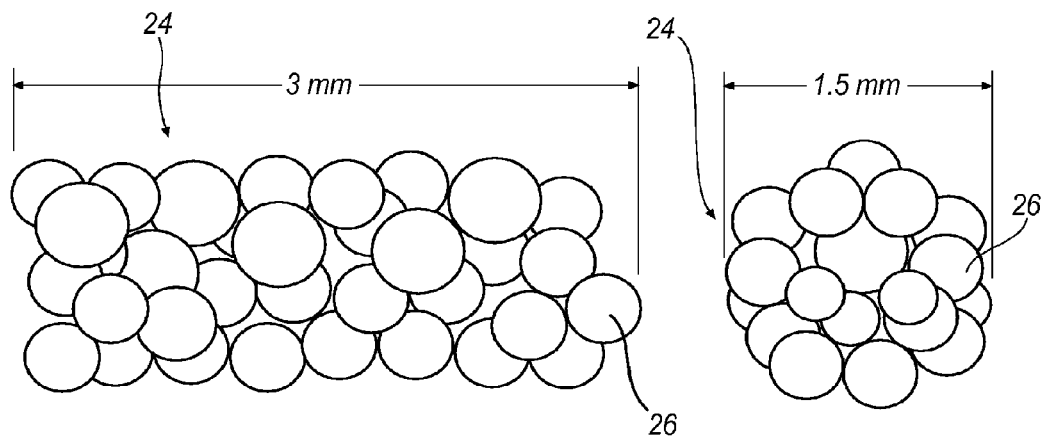
FIG. 2A is a side elevational view of a site marker according to a first embodiment of the present invention.
FIG. 2B is an end elevational view of the site marker of FIG. 2A.

Referring initially to FIGS. 2A and 2B, a site marker 24 includes a plurality of balls 26 sintered together to form a unitary body. The balls 26, as shown, vary in size and are sintered together randomly such that there is no structured or predetermined equidistance between the centers of the balls 26. In other embodiments, the size of the balls 26 may be generally uniform, or the balls 26 may be sintered together such that the centers of the balls 26 are aligned in a predetermined manner. As illustrated in FIGS. 2A and 2B, one embodiment of site marker 24 measures approximately 1.5 mm in diameter (FIG. 2B) and 3 mm in length (FIG. 2A). As those skilled in the art will appreciate, when the size and sintering pattern of the balls 26 are modified, the size, shape and dimensions of the site marker will also vary. The balls 26 may be constructed from any biocompatible material with suitable echogenic properties such as, but not limited to, titanium, stainless steel, or platinum.

Figures 3A, 3B:
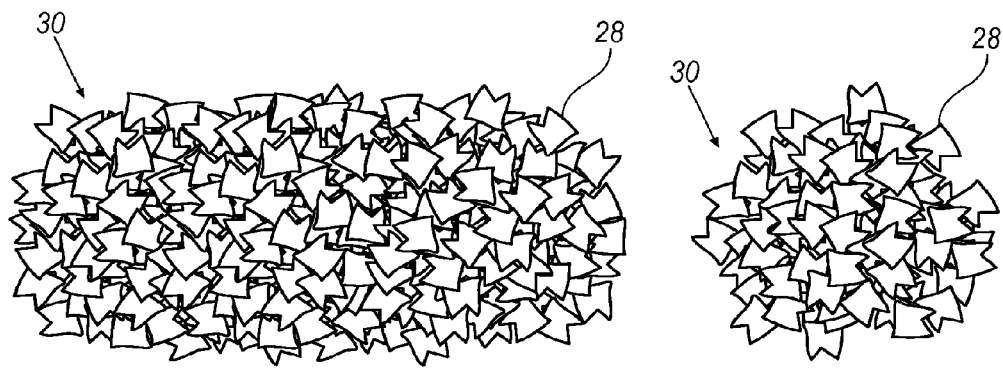
FIG. 3A is a side elevational view of a site marker according to a second embodiment of the present invention.
FIG. 3B is an end elevational view of the site marker of FIG. 3A.

FIGS. 3A and 3B illustrate another embodiment of the invention having irregularly shaped particles or bits 28 that are sintered together to form site marker 30. The particles, as shown in FIGS. 3A and 3B, are exaggerated to illustrate the random shapes of the particles 28. In application, however, the edges of the particles are sufficiently smooth so as to not damage any tissue. The particles can be substantially similar in size and shape, or they may vary as shown in FIGS. 3A and 3B. The particles 28 may be constructed from any biocompatible material with suitable echogenic properties such as, but not limited to, titanium, stainless steel, or platinum.

In another aspect of the invention, the particles 28 may be sufficiently small such that, when sintered together, the resultant site marker 32 appears to form a porous metal, as shown in FIGS. 4A and 4B.

FIG. 5 shows another embodiment of a biopsy site marker 34 made from a continuous strand of wire 36. To form the biopsy site marker 34, the wire 36 is fed into a molding cavity (not shown). When the wire 36 reaches the back wall of the cavity, it folds over onto itself conforming to the shape of the molding cavity. The wire 36 is compressed into a mass that resembles a ball of yarn. Inherently, the size and shape of the site marker 34 is dependent upon the size and shape of the molding cavity. The wire 36 may be constructed from any biocompatible material with suitable echogenic properties such as, but not limited to, titanium, stainless steel, or platinum.

Figure 6:
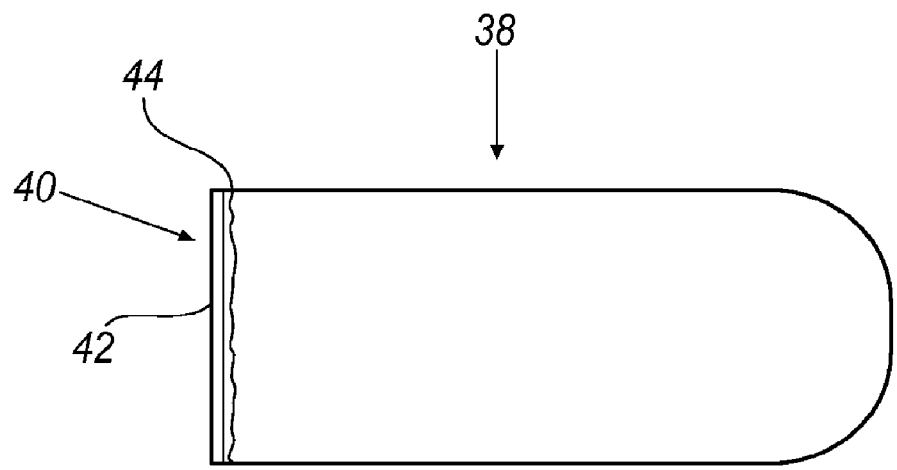
FIG. 6 is a side elevational view of a site marker according to a fifth embodiment of the present invention.
Figure 6A:
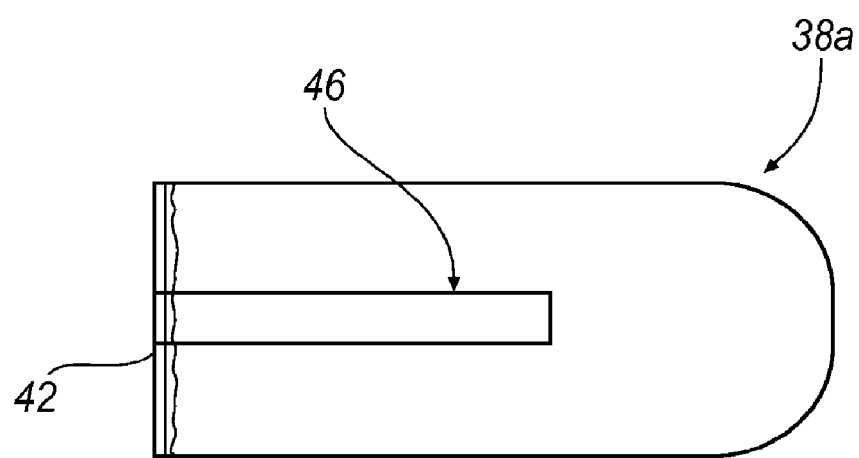
FIG. 6A is a side elevational view of a site marker according to a sixth embodiment of the present invention.

FIG. 6 shows a thin-walled hollow site marker in the form of a capsule 38 having an open end 40. A cap 42 is attached to the open end 40 by a weld 44. The capsule 38 is designed to resonate at a predetermined ultrasound frequency. In the event that the capsule 38 needs to resonate at more than one frequency, a resonant beam 46, as shown in FIG. 6A, can be attached to the inner surface wall of the cap 42 so that the beam resonance is transmitted through the wall of the capsule. The capsule 38 may be constructed from any biocompatible material with suitable echogenic properties such as, but not limited to, titanium, stainless steel, or platinum.

Figure 7:
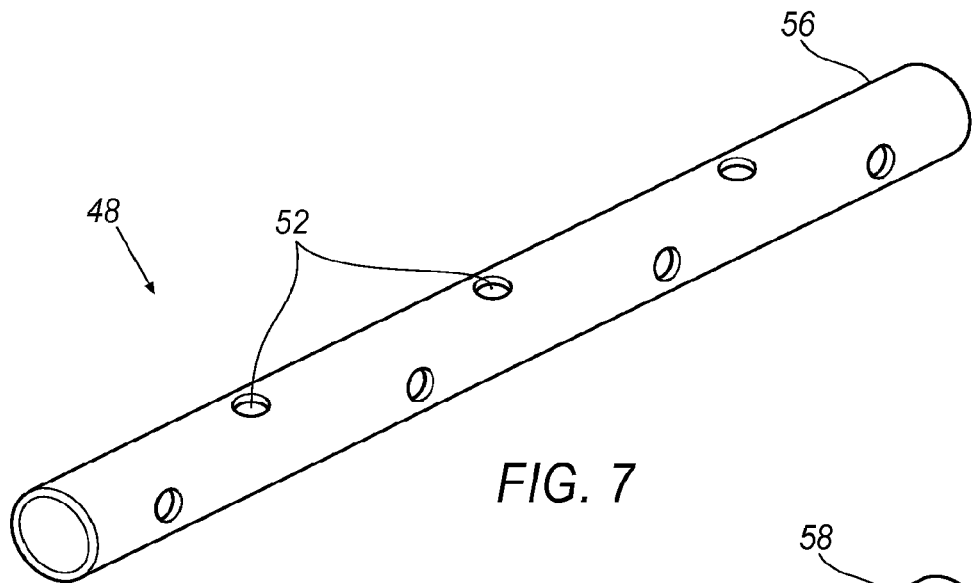
FIG. 7 is a perspective view of a site marker according to a seventh embodiment of the present invention.
Figure 7A:
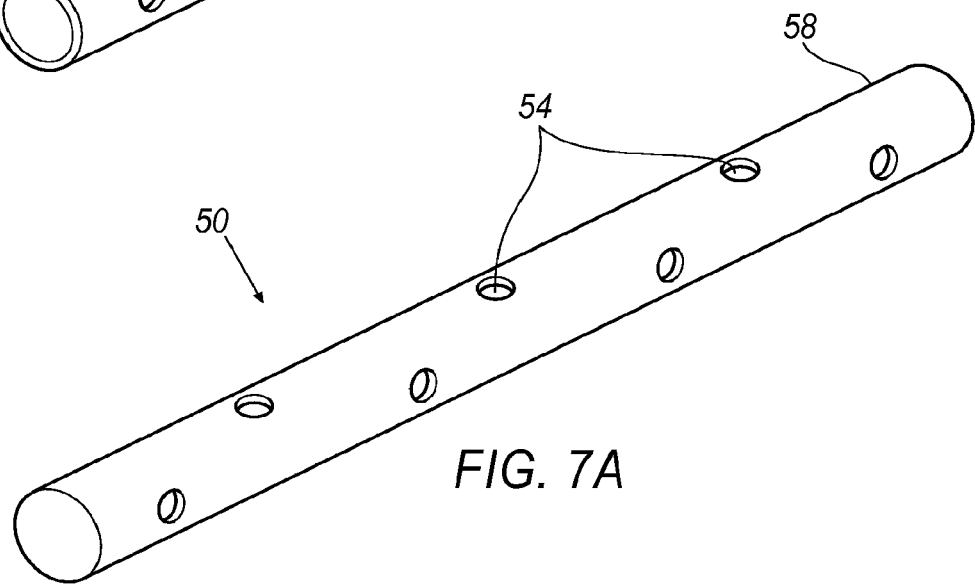
FIG. 7A is a perspective view of a site marker according to an eighth embodiment of the present invention.

FIGS. 7 and 7A show site marker 48, 50 in the form of a rod 56, 58 having drilled holes 52, 54 throughout the body of the rod. Site marker 48 of FIG. 7A is a solid rod, whereas site marker 50 of FIG. 7 is a hollow rod or tube. The holes in both rods 48, 50 may be drilled in a random or in a predetermined pattern. The rod 56, 58 may be constructed from any biocompatible material with suitable echogenic properties such as, but not limited to, titanium, stainless steel, or platinum.

Figure 8A:
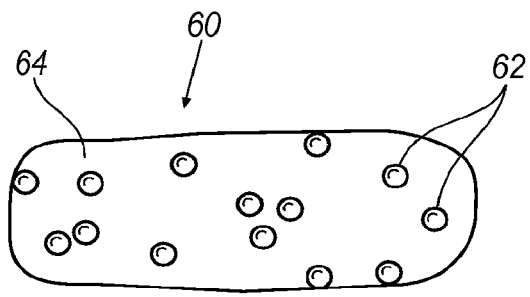
FIG. 8A is a side elevational view of a site marker according to a ninth embodiment of the present invention.
Figure 8B:
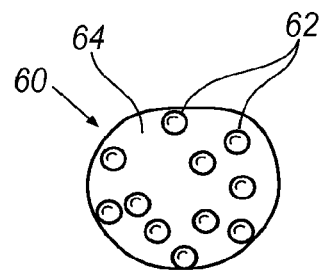
FIG. 8B is an end elevational view of the site marker of FIG. 8A.

FIGS. 8A and 8B illustrate another embodiment of a site marker 60 that includes ball or bits 62 of material that are visible under one or more imaging modalities, and dispersed in a block of material 64 that is different than the balls or bits 62. The balls or bits 62 may be constructed of titanium, stainless steel or other suitable material that are visible under more than one imaging modalities. In addition, the balls or bits 62 of material may be contacting each other within the block 64 and may vary in size and shape. In one embodiment, the block of material 64 is a biocompatible material such as epoxy. In another embodiment, the block of material is constructed of a bioabsorbable material that is absorbed by the patient's body such that only the balls 62 remain at the biopsy site.

Figure 9:
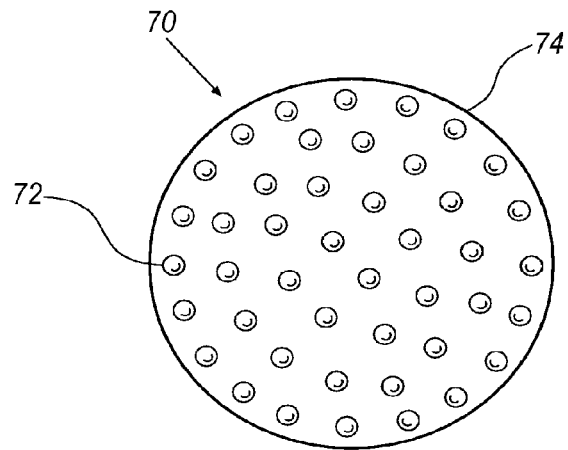
FIG. 9 is a side elevational view of a site marker in accordance with a tenth embodiment of the present invention.

FIG. 9 illustrates another embodiment of a site marker 70 that is made in accordance with the present invention. Site marker 70 is a unitary body made of biocompatible material or a combination of biocompatible materials that are visible under one or more imaging modalities. Marker 70 may be hollow or solid. According to one aspect of the invention, marker 70 further includes a plurality of depressions 72 formed on an outer surface 74 of marker 70. Depressions 72 may be formed on surface 74 so as to be set a predetermined distances apart from one another or may be randomly formed on outer surface 74. Depressions 72 may also be formed so as to have a variety of shapes. In one embodiment, depressions 72 have a parabola shape, with a length of at least about 0.25 mm.

Figure 10A:
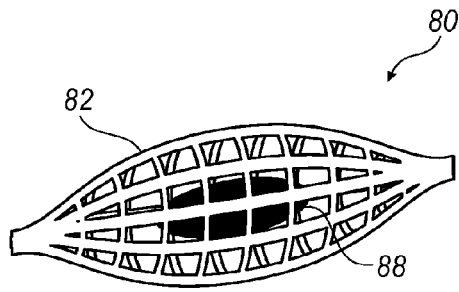
FIG. 10A is a side elevational view of a site marker in accordance with an eleventh embodiment of the present invention.

In another embodiment, FIG. 10A discloses yet another alternative embodiment of a site marker 80. Site marker 80 includes a generally hollow body portion 82 that is flanked by closed ends 84, 86. Positioned within body portion 82 is a smaller permanent marker 88 that is captured therein. However, permanent marker 88 need not be attached to body portion 82 in any way. Permanent marker is preferably constructed of a suitable material that will not biodegrade within the body and which may be viewed under multiple imaging modalities, such as Magnetic Resonance Imaging (MRI). Examples of suitable materials for permanent marker 88 include, but are not limited to, titanium, stainless steel, ceramic, carbon, nickel titanium, and glass.

In one embodiment, body portion 82 is constructed of a bioabsorbable material such as polyglycolic acid (PGA), polylactic acid (PLA), hydrogel, collegen-based material or any other suitable material. The bioabsorbable material may be woven into a flexible mesh that has openings formed therein that are sized so as to be smaller than permanent marker 88 such that permanent marker 88 cannot escape body portion 82. After installation in a biopsy cavity, over a predetermined time period such as three weeks to six months, body portion 82 is absorbed by the body, such that only permanent marker 88 remains within the body at the biopsy cavity. Because permanent marker 88 is captured within body portion 82 prior to absorption thereof by the body, permanent marker 88 is restricted from migrating from within the biopsy cavity. Indeed, movement of permanent marker 88 is limited to the internal cavity defined by body portion 82. This insures that permanent marker 88 remains within the biopsy cavity to permit follow-up imaging of the biopsy site.

Figure 10B:
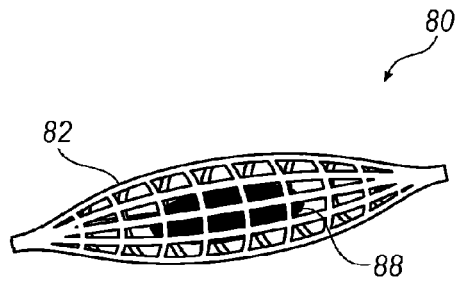
FIG. 10B is a side elevational view of the site marker of FIG. 10A in a pre-deployment configuration.

In one embodiment, prior to deployment into the biopsy site by a suitable deployment mechanism, site marker 80, and more specifically, body portion 82 is formed in a first pre-deployment configuration (as shown in FIG. 10B), whereby the site marker 80 is compressed into a predetermined size and shape so as to be readily positionable within the deployment device. In fact, site marker 80 may be positioned in the deployment device prior to shipping deployment device. Once site marker 80 exits the deployment device into the biopsy site, site marker 80 is released from its compressed first pre-deployment configuration and automatically expands into a second post-deployment configuration (shown in FIG. 10A), whereby at least a portion of the body portion 82 of the site marker 80 expands at least as much as the outside diameter of the deployment device to form a close cage that holds permanent marker 88 such that site marker 80 cannot migrate back into the deployment device.

Figure 10C:
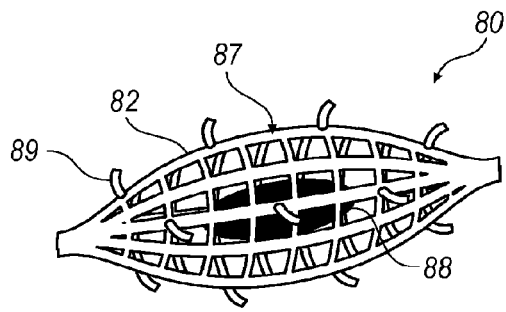
FIG. 10C is a side elevational view of a site marker in accordance with a twelfth embodiment of the present invention.

In another embodiment, as shown in FIG. 10C, an outside surface 87 of body portion 82 is provided with one or more barbs 89 disposed thereon. The barbs 89 assist in adhering site marker 80 to internal walls of the biopsy cavity. Barbs 89 are configured so as to extend at a predetermined angle relative to outside surface 87. In one specific embodiment, barbs 89 are configured to extend perpendicular to outside surface 87. In another embodiment, barbs 89 are positioned at different angles relative to one another, including opposing one another.

Figure 10D:
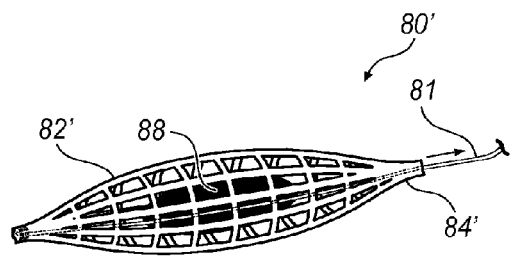
FIG. 10D is a side elevational view of a site marker in a pre-deployment position in accordance with a thirteenth embodiment of the present invention.
Figure 10E:
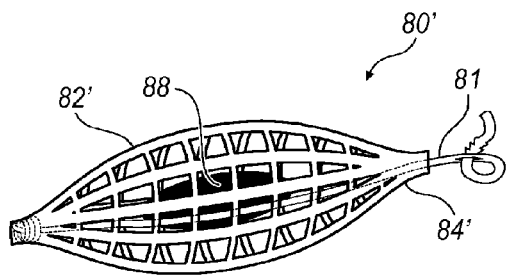
FIG. 10E is a side elevational view of the site marker of FIG. 10D in a post-deployment position.

In another embodiment, as shown in FIGS. 10D and 10E, body portion 82' of site marker 80' is manually expanded from a first pre-deployment configuration (FIG. 10D) into a second post-deployment configuration (FIG. 10E). In this embodiment, site marker 80' is provided with a thread 81 or deployment line (e.g., thread, filament, wire) that is attached to the forward end 84' of body portion 82'. Thread 81 is held by a tie-wrap style clinch via the deployment device. Once the site marker 80' is deployed, the tie-wrap pulls on thread 81 which pops open body portion 82' to the second post-deployment device to a predetermined maximum size. Upon reaching the predetermined maximum size, the deployment device severs thread 81, releasing site marker 80' into the biopsy site.

Figure 11A:
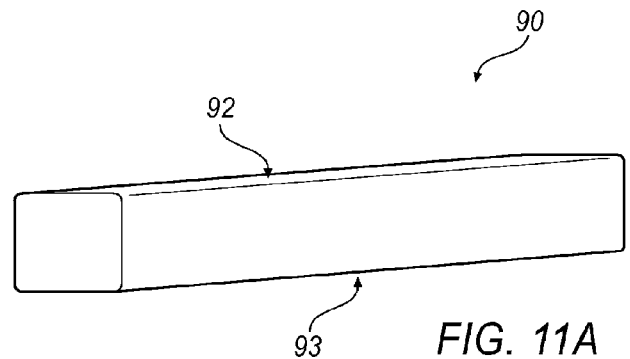
FIG. 11A is a side elevational view of a site marker in accordance with a fourteenth embodiment of the present invention.
Figure 11B:
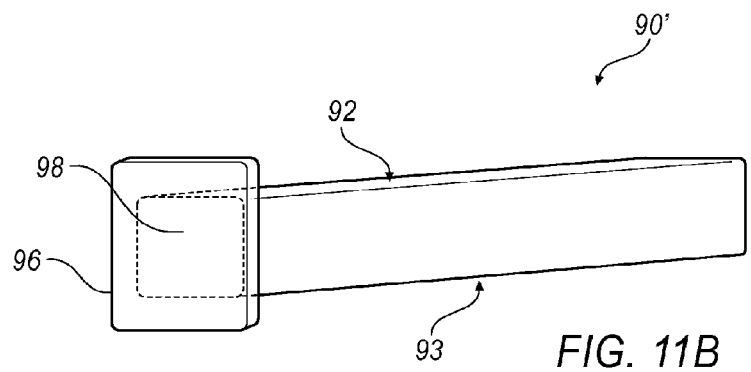
FIG. 11B is a side elevational view of a site marker in accordance with a fifteenth embodiment of the present invention.

Another embodiment of a site marker 90 is shown in FIGS. 11A and 11B. Site marker 90 is formed as a solid beam defined by relatively planar top and bottom surfaces 92 and 93. When site marker 90 is subjected to a predetermined ultrasound frequency, it resonates, thereby making it visible under various modalities.

In an alternative embodiment, as shown in FIG. 11B, site marker 90' may further include a flange 96 attached to an end portion 98 the site marker 90 to assist with deployment and/or positioning site marker 90' within the biopsy site.

In one embodiment, site marker 90, 90' and flange 96 is constructed from titanium or other 7uitable material. In another embodiment, site marker 90, 90' is constructed from a solid piece of material such that it has no sealed chambers or regions that contain gas or air.

In yet another site marker design, the site marker contains a plurality of solid glass beads that are fused together similar to the sintered site marker 24 described above in connection with FIGS. 2A and 2B. In one embodiment, the glass material has a specific acoustic impedance ratio in the range of 8.2-9.4. The glass balls are fused together such that there are no sealed chambers or regions that contain air or gas.

Figure 12A:
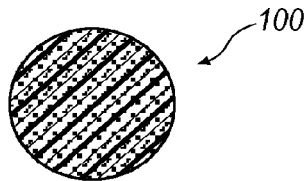
FIG. 12A is a side elevational view of a site marker in accordance with a sixteenth embodiment of the present invention.
Figure 12B:
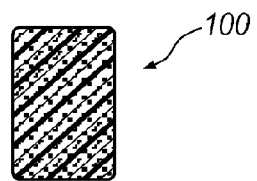
FIG. 12B is an end view of the site marker of FIG. 12A in a pre-deployment position.
Figure 12C:
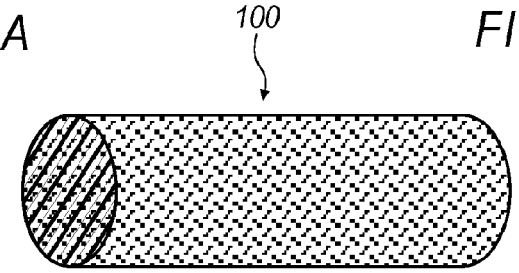
FIG. 12C is a side elevational view of the site marker of FIG. 12A in a post-deployment position.

FIG. 12A-12C depict a site marker 100 that is constructed of a foam-like material. The foam-like material may be a carbon filled polymer or a glass filled polymer so as to be visible under multiple modalities. In addition, the foam-like material may contain therapeutic materials to deliver medication to the biopsy site. One exemplary material for construction of site marker 100 is a thrombin filled polymer. The foam-like material acts as a matrix for tissue ingrowth.

Site marker 100 expands from a first pre-deployment configuration (shown in FIG. 12B) to a second post-deployment configuration (shown in FIG. 12C). In the first pre-deployment configuration, site marker is substantially compressed in either length or width or both so as to be receivable within a suitable deployment device. The site marker may remain in the pre-deployment device for an extended period of time, such that it may be desirable to pre-load a deployment device with one or more of the site markers in the first pre-deployment configuration.

In one embodiment, the material may from which site marker 100 is constructed is a shape memory material that will spring into the second post deployment configuration upon release from a deployment device into a biopsy cavity. In accordance with this embodiment, the site marker is designed to have a predetermined shape and then compressed into the first pre-deployment configuration. The site marker is then retained in the first pre-deployment configuration and may be loaded into a deployment device. It should be noted that the site marker may be stored in the deployment device in the first pre-deployment configuration for an extended period of time.

Once released from the deployment device and into the biopsy cavity, the site marker automatically springs into the second post-deployment configuration having a predetermined size and shape such that the site marker is easily visible under various imaging modalities.

In another embodiment, site marker 100 is constructed of a temperature dependent material. In accordance with this embodiment, the site marker does not expand from the first pre-deployment configuration into the second post-deployment configuration until heat is applied to the site marker 100. Deploying the site marker 100 into a biopsy cavity provides a sufficient level of heat generated from the body to enable site marker 100 to automatically expand into the second post-deployment configuration after deployment.

Figure 13A:
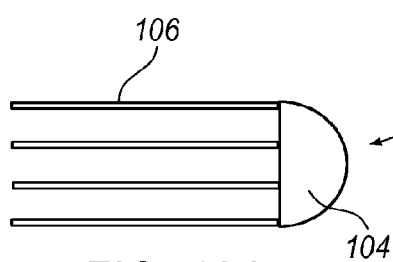
FIGS. 13A-13B are side views of a site marker in accordance with a seventeenth embodiment of the present invention.
Figure 13B:
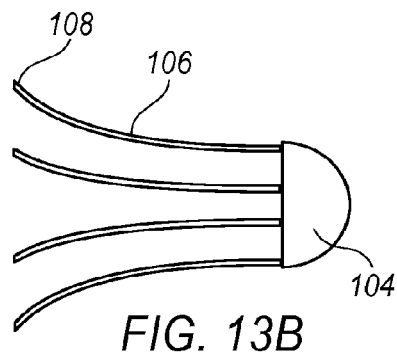

In another embodiment, shown in FIGS. 13A-13B, a site marker 102 having a marker head 104 and one or more appendages 106 attached thereto is disclosed. In this embodiment, the marker head 104 may be a permanent marker such that it will not become absorbed by the body after deployment. Alternatively, however, it is understood that marker head 104 may be a bioabsorbable marker that is absorbed by the body by a predetermined time.

In one embodiment, the appendages 106 attached to the marker head 104 are semi-rigid and constructed of a heat activated material that causes the appendages 106 to curl outwardly once received in the body (See FIG. 13B). These appendages 106 serve to contact the walls of a biopsy cavity to prevent the marker 102 from migrating outside of the biopsy cavity.

Alternatively, the appendages 106 may be constructed of a memory-shape material whereby the appendages 106 are preformed with curled, outwardly extending ends 108. The appendages 106 are then compressed into a pre-deployment configuration, such as that shown in FIG. 13A to enable the marker 102 to be received within and deployed from a suitable deployment device. Once the marker 102 is deployed, the appendages 106 resume its preformed configuration which enables the appendages 106 to engage the walls of a biopsy cavity to prevent the marker 102 from migrating.

Figure 13C:
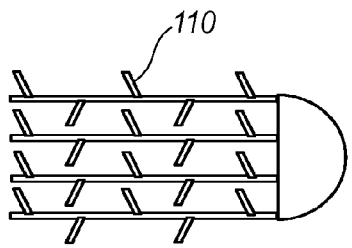
FIG. 13C is a side view of a site marker in accordance with a eighteenth embodiment of the present invention.

In another embodiment, as shown in FIG. 13C, appendages 106 may include one or more barbs 110 that extend outwardly from appendages 106. Barbs 110 may be angled relative to appendages 106 and may be arranged on both top and bottom surfaces of appendages 106. While FIG. 13C illustrates barbs 110 being angled in a first direction on a top surface of appendages 106 and a second direction on a bottom surface of appendages 106, it is understood that barbs 110 be oriented on each surface of appendages 106 in multiple directions. Barbs 110 serve to aid in attaching marker 102 to the walls of a biopsy cavity.

Figure 13D:
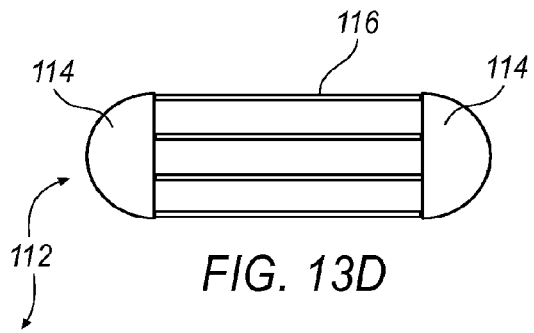
FIGS. 13D-13E are side views of a site marker in accordance with an nineteenth embodiment of the present invention.
Figure 13E:
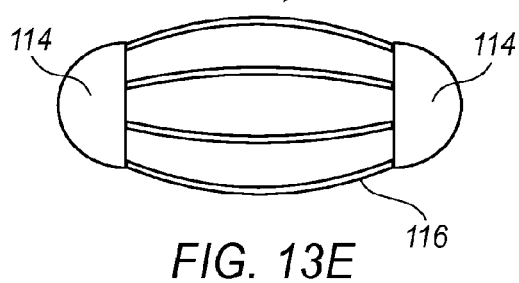

FIGS. 13D and 13E are still a further embodiment of a site marker 112. In this embodiment, site marker 112 includes two marker heads 114 that are joined together by one or more appendages 116. The appendages 116 may include barbs (not shown) and may deform after deployment to a bowed configuration (FIG. 13E) to engage the biopsy cavity and prevent migration.

Figure 14A:
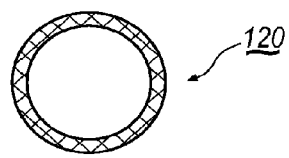
FIG. 14A is a front view of a site marker in accordance with a twentieth embodiment of the present invention.
Figure 14B:
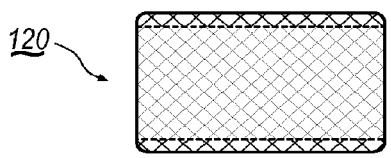
FIG. 14B is a side view of the site marker of FIG. 14A.
Figure 14C:
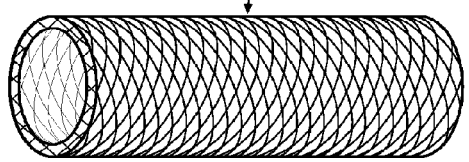
FIG. 14C is a side elevational view of the site marker of FIG. 14A.

In another embodiment of the present invention, shown in FIGS. 14A-14C, an expandable site marker 120 is disclosed. Site marker 120 is generally hollow, defining a passageway therethrough and is constructed of a stent-like, woven mesh material that acts as a matrix for tissue ingrowth. The site marker 120 expands from a first pre-deployment configuration (shown in FIG. 14B) to a second, larger post-deployment configuration (shown in FIG. 14C). In the first pre-deployment configuration, site marker is substantially compressed in either length or width or both so as to be receivable within a suitable deployment device. The site marker 120 may remain in the pre-deployment device for an extended period of time, such that it may be desirable to pre-load a deployment device with one or more of the site markers 120 in the first pre-deployment configuration.

In one embodiment, the material may from which site marker 120 is constructed is a shape memory material that will spring into the second post deployment configuration upon release from a deployment device into a biopsy cavity. In accordance with this embodiment, the site marker 120 is designed to have a predetermined shape and then compressed into the first pre-deployment configuration. The site marker 120 is then retained in the first pre-deployment configuration and may be loaded into a deployment device. It should be noted that the site marker 120 may be stored in the deployment device in the first pre-deployment configuration for an extended period of time.

Once released from the deployment device and into the biopsy cavity, the site marker 120 automatically springs into the second post-deployment configuration having a predetermined size and shape such that the site marker 120 is easily visible under various imaging modalities.

In another embodiment, site marker 120 is constructed of a temperature dependent material. In accordance with this embodiment, the site marker 120 does not expand from the first pre-deployment configuration into the second post-deployment configuration until heat is applied to the site marker 120. However, deploying the site marker 120 into a biopsy cavity provides a sufficient level of heat generated from the body to enable site marker 120 to automatically expand into the second post-deployment configuration after deployment.

Figure 15A:
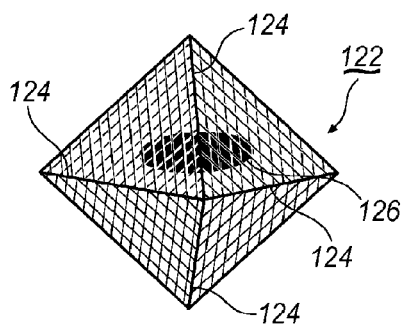
FIG. 15A is a side elevational view of a site marker in accordance with a twenty first embodiment of the present invention.

Yet another embodiment of a site marker 122, is shown in FIG. 15A. When site marker 122 is in a deployed configuration, as shown in FIG. 15A, it has a tetrahedron shell defined by external spines or ribs 124 that are pre-biased so as to form the tetrahedron shape. The spines 124 are connected together by a woven web material that permits tissue ingrowth to create the tetrahedron shell In one embodiment, tetrahedron shell is bioabsorbable such that after a predetermined time, the shell is completely absorbed by the body.

Contained within the tetrahedron shell is a marker 126 that is visible under one or more modalities. By having the marker 126 contained within the shell, the marker 126 is prevented from migrating. Indeed, the marker 126 may only move within the shell. In one embodiment, marker 126 is a permanent marker that will not become absorbed by the body. Alternatively, marker 126 may be a non-permanent marker that remains within the body for a predetermined length of time.

Figure 15B:
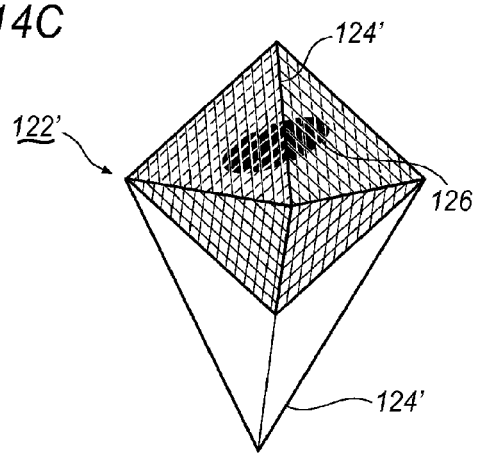
FIG. 15B is a side elevational view of a site marker in accordance with a twenty second embodiment of the present invention.

In an alternative embodiment, site marker 122' may be formed to have a double tetrahedron shell as shown in FIG. 15B. The double tetrahedron site marker 122' design is similar to the single tetrahedron site marker 122 in that it also is defined by external spines 124' that are pre-biased into the deployed configuration, as shown in FIG. 15B.

Figure 15C:
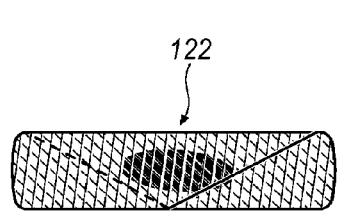
FIG. 15C is a side view of the site markers of FIGS. 15A and 15B in a pre-deployment position.

Both site marker 122 and 122' may be compressed into a first pre-deployment configuration, such as that shown in FIG. 15C. In this configuration, site markers 122 and 122' are substantially compressed in either length or width or both so as to be receivable within a suitable deployment device. The site markers 122 and 122' may remain in the pre-deployment device for an extended period of time, such that it may be desirable to pre-load a deployment device with one or more of the site markers 122 or 122' in the first pre-deployment configuration.

Once deployed by a suitable deployment device or released from the first, pre-deployed configuration, the pre-biased spines 124, 124' of site markers 122 and 122' automatically return to site markers 122 and 122' to the deployed configurations shown in FIGS. 15A and 15B.

Figure 15D:
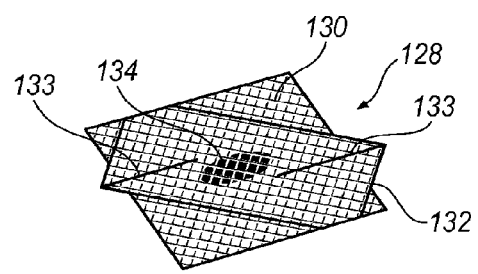
FIG. 15D is a side elevational view of a site marker in accordance with a twenty third embodiment of the present invention.

Yet another embodiment of a site marker 128 is shown in FIG. 15D. In this embodiment, a tube 130 that is formed of a mesh-like material is provided. Internal spines 132, including base spines 133, are positioned within tube 130 that are pre-biased to form a tetrahedron shell within tube 130 when in a deployed configuration. A marker 134 is positioned within the tetrahedron shell such that the marker is prevented from undesirable migration within the biopsy cavity.

In yet another alternative embodiment, base spines 133 are eliminated such that the remaining spines 132 within tube 130 are biased to form capped ends when the site marker 128 is in a deployed configuration.

To deploy the embodiments described in connection with FIG. 15D, the site marker 128 must be compressed into suitable size and shape to enable it to be received, stored and translated within a deployment device. Once the site marker 128 is deployed from the device, the pre-biased internal spines 132 and 133, will automatically return the site marker 128 into the deployed configuration.

Figure 16A:
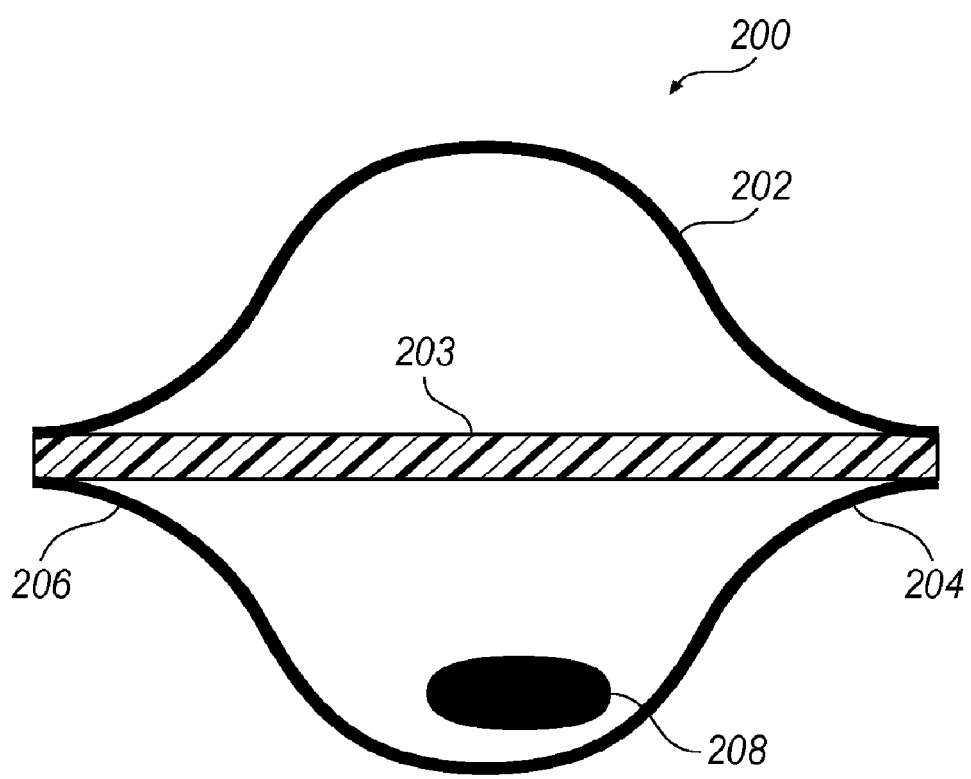
FIG. 16A is a partial cross section of if the site marker of FIG. 10E in a post-deployment position.

FIG. 16A illustrates a partial cross sectional view of another embodiment of a site marker 200 that is similar to the embodiment shown in FIG. 10E. Site marker 200 includes a body portion 202, which is shown in a post-deployment configuration. In this embodiment, site marker 200 is provided with a thread 203 or deployment line (e.g., thread, filament, wire) that is attached to and extends between a forward end 204 and a rearward end 206 of body portion 202. Body portion 202 of site marker 200 is manually expanded from a first pre-deployment configuration (i.e., FIG. 10D) into the second post-deployment configuration by thread 203 or deployment line. More specifically, thread 203 is pre-biased to spring forward and rearward ends 204, 206 away from on another. A permanent marker 208 is positioned within body portion 202 and need not be attached to body portion 202 in any way. Instead, marker 208 may float freely within body portion 202.

Figure 16B:
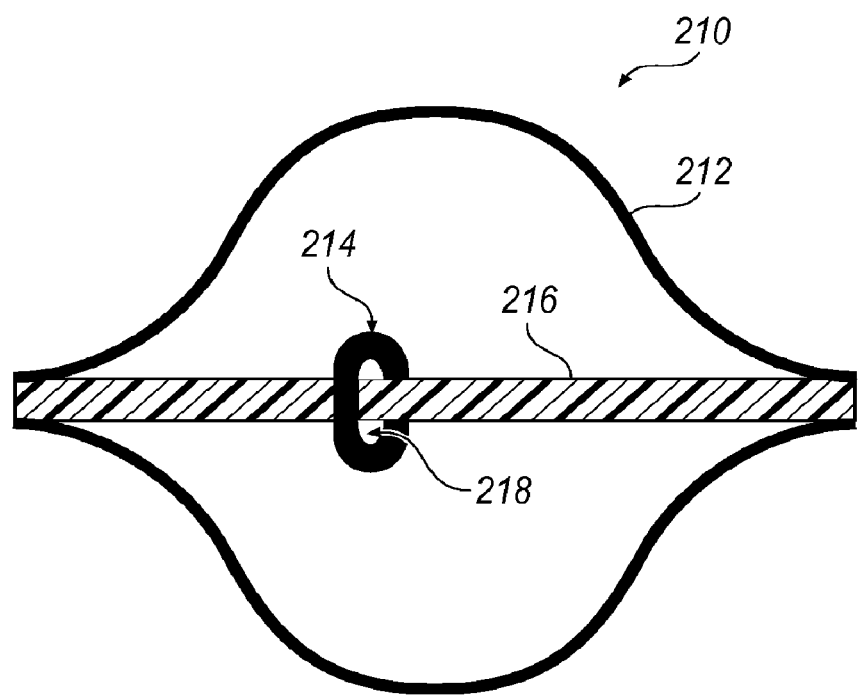
FIG. 16B is a partial cross sectional view of a site marker in a post-deployment position, with the permanent marker shown in perspective view, in accordance with a twenty fourth embodiment of the present invention.

In yet another embodiment of a site marker 210, as shown in FIG. 16B, a body portion 212 has at least one marker 214 that is held in place by deployment line 216. Marker 214, which may be a permanent marker that does not break down and become absorbed by the body for a predetermined time period, includes a through hole 218. Accordingly, deployment line 216 is received in through hole 218 such that marker 214 may selectively slide along deployment line 216. While marker 214 is shown as having a donut shape, it is understood that any body with a through hole able to accommodate the deployment line 216 such as, but not limited to, a ring, helical shape or tube that is able to slide along deployment line 216 without departing from the invention. In one embodiment, after installation in a biopsy cavity, over a predetermined time period such as three weeks to six months, body portion 212 is absorbed by the body, such that only marker 214 remains within the body at the biopsy cavity, and is visible under one or more modalities.

As mentioned above, marker 214 may be a permanent marker that is not absorbed by the body. Alternatively, marker 214 may be a semi-permanent marker that absorbs slower than body portion 212. Because the movement of marker 214 is restricted by deployment line 216 prior to absorption thereof by the body, marker 214 is restricted from migrating from within the biopsy cavity. Indeed, movement of marker 214 is limited along the deployment line 216. This insures that marker 214 remains within the biopsy cavity to permit follow-up imaging of the biopsy site.

Figure 16C:
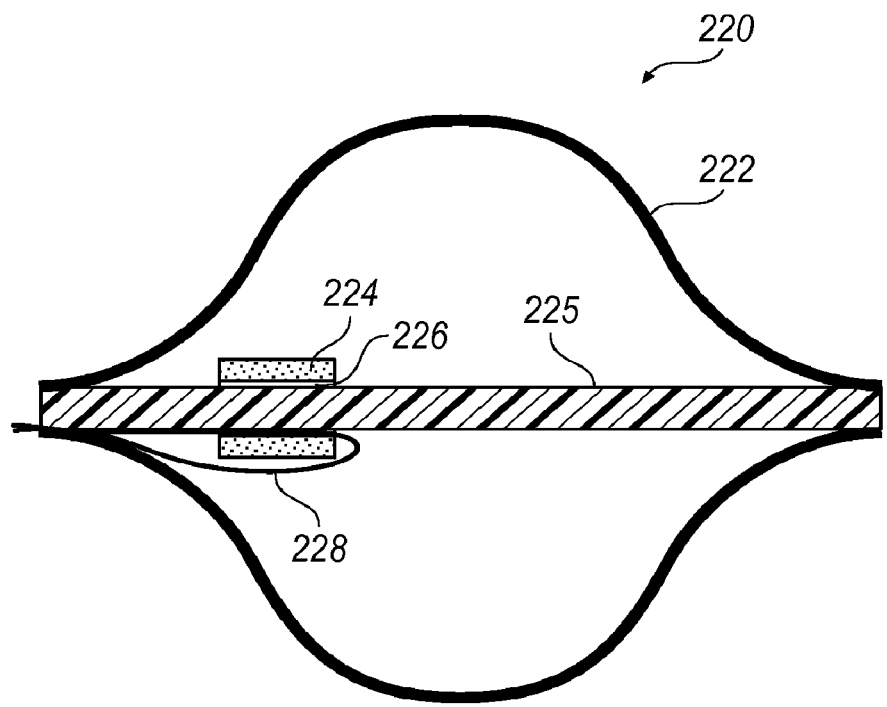
FIG. 16C is a partial cross sectional view of a site marker in a post-deployment position in accordance with a twenty fifth embodiment of the present invention.

In yet another alternative embodiment, a site marker 220, as shown in FIG. 16C, includes a body portion 222 and at least one marker element 224. Similar to the embodiment depicted in FIG. 16B, marker element 224 includes a through hole 226 that receives a deployment line 225. In the embodiment shown, marker element 224 has an elongated profile, similar to a tube. However, it is understood that other shapes of marker 224 may be utilized. Marker element 224 may be at least partially retained by a filament 228, where filament 228 is bonded to an end of body portion 222. In one embodiment, filament 228 forms a loop around a portion of marker element 224, to hold marker 224 in position within body portion 222 in addition to deployment line 225.

After installation in a biopsy cavity, over a predetermined time period such as three weeks to six months, body portion 222 is absorbed by the body, such that only marker 224 remains within the body at the biopsy cavity. Because marker 224 is restricted along deployment line 225, and is further constrained by filament 228, marker 224 is restricted from migrating from within the biopsy cavity. Indeed, movement of marker 224 is limited along the deployment line 225 and is further constrained by filament 228. This insures that marker 224 remains within the biopsy cavity to permit follow-up imaging of the biopsy site.

Figure 16D:
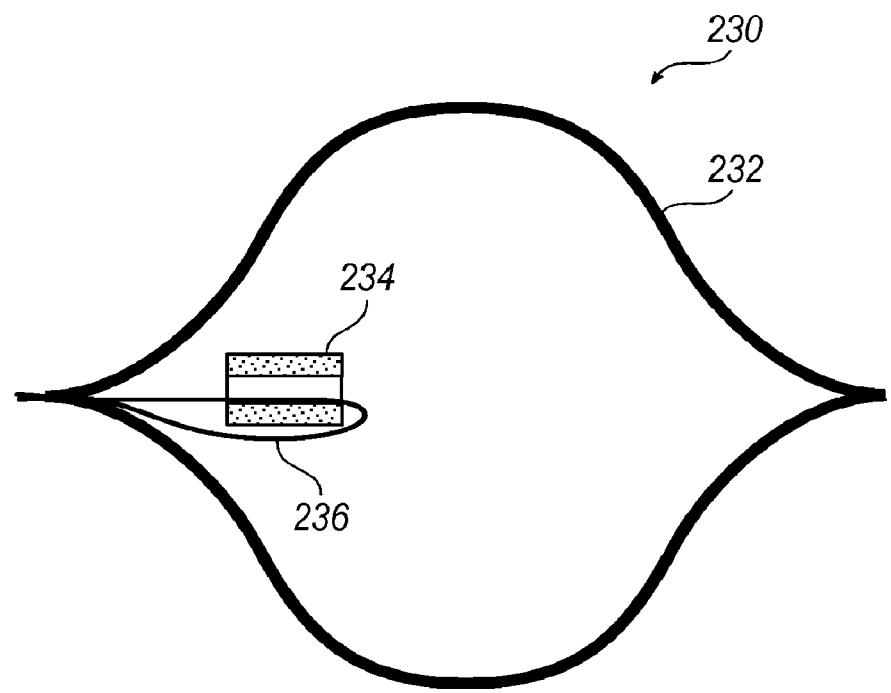
FIG. 16D is a partial cross sectional view of a site marker in a post-deployment position in accordance with a twenty sixth embodiment of the present invention.

Yet another embodiment of a site marker 230 is shown in FIG. 16D. Site marker 230 includes a body portion 232 and at least one marker element 234. In this embodiment, marker element 234 is restrained only by filament 236. Once site marker 230 exits a deployment device into the biopsy site, site marker 230 is released from a pre-biased and compressed first pre-deployment configuration and automatically expands into a second post-deployment configuration (shown in FIG. 16D). Because marker 234 is restricted by filament 236, marker 234 is restricted from migrating from within the biopsy cavity. Indeed, movement of marker 234 is limited along filament 236. This insures that marker 234 remains within the biopsy cavity to permit follow-up imaging of the biopsy site.

Figure 16E:
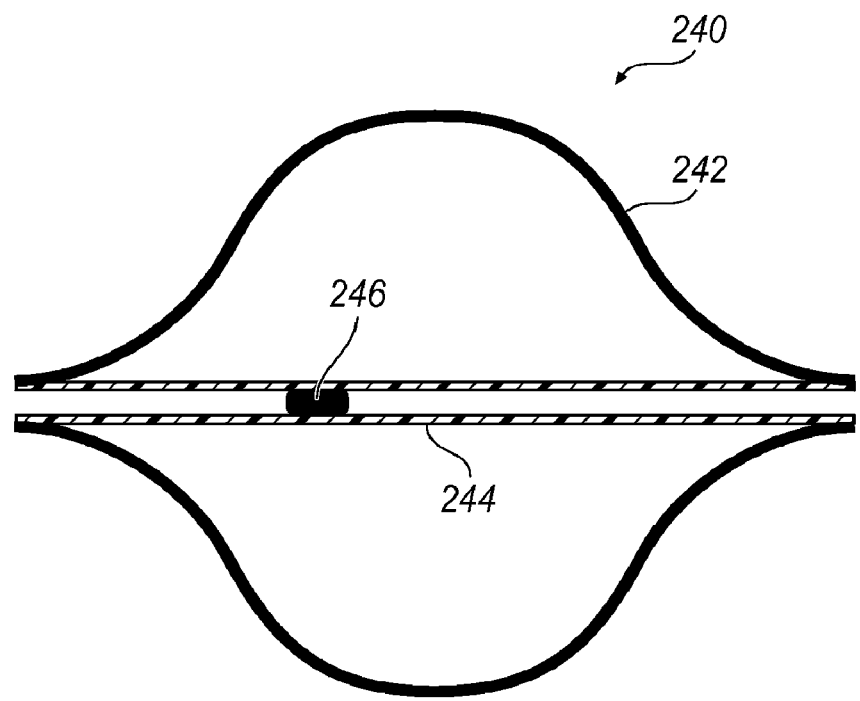
FIG. 16E is a partial cross sectional view of a site marker in a post deployment position, with a partial cross sectional view of the deployment line in accordance with a twenty seventh embodiment of the present invention.

In yet another embodiment of a site marker 240, as shown in FIG. 16E, includes a body portion 242 that has a hollow deployment line 244. Deployment line 244, which is shown in cross sectional view, is designed so as to be able to accommodate at least one marker 246. Marker 246 is constructed such that it has a smaller outside periphery than the inner circumference of hollow deployment line 244. Marker 246 is able to selectively slide inside of hollow deployment line 244. Because the movement of marker 246 is restricted by hollow deployment line 244 prior to absorption thereof by the body, marker 246 is restricted from migrating from within the biopsy cavity. Indeed, movement of marker 246 is limited along hollow deployment line 244. This insures that marker 246 remains within the biopsy cavity to permit follow-up imaging of the biopsy site.

While the present invention has been particularly shown and described with reference to the foregoing preferred embodiments, it should be understood by those skilled in the art that various alternatives to the embodiments of the invention described herein may be employed in practicing the invention without departing from the spirit and scope of the invention as defined in the following claims. It is intended that the following claims define the scope of the invention embodiments within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. A site marker, comprising:
   a generally hollow, bioabsorbable body portion having a substantially closed configuration that defines a cavity therein;
   a filament secured to an end of said body portion; and
   at least one marker element located within the cavity, wherein said filament is secured to said marker element, thereby limiting migration of said marker element.

2. The site marker of claim 1, wherein said filament is formed into a loop that is received within a through hole formed through said at least one marker element.

3. The site marker of claim 1, wherein said filament has a predetermined length such that said at least one marker element is retained closer to one end of said body portion.

4. The site marker of claim 1, wherein said bioabsorbable material is one of polyglycolic acid, polylactic acid, hydrogel, and collagen-based material.

5. The site marker of claim 1, wherein said body portion is absorbed by a mammalian body after a predetermined time period.

6. The site marker of claim 1, wherein said at least one marker element is permanent and not bioabsorbable.

7. The site marker of claim 6, wherein said at least one marker element is visible under multiple imaging modalities.

8. The site marker of claim 1, wherein said filament extends through said at least one marker element.

9. The site marker of claim 1, further comprising a deployment line that extends through said at least one marker element.

10. The site marker of claim 9, wherein the deployment line is secured to a first end of the body portion and is configured to alter the length between the first end and a second end of the body portion to change the site marker from a pre-deployment configuration to a post-deployment configuration.

* * * * *